United States Patent [19]
Matsui et al.

[11] 4,153,727
[45] May 8, 1979

[54] PHARMACEUTICAL COMPOSITIONS OF A PROSTAGLANDIN COMPOUND FOR RECTAL USE IN TREATING ASTHMA

[75] Inventors: Hidefumi Matsui, Kitamoto; Kenichi Tomioka, Okegawa; Hiroitsu Kawada, Kawagoe; Hiroo Maeno, Shiki, all of Japan

[73] Assignee: Yamanouchi Pharmaceutical Co., Ltd., Tokyo, Japan

[21] Appl. No.: 867,932

[22] Filed: Jan. 9, 1978

[30] Foreign Application Priority Data

Jan. 20, 1977 [JP] Japan ................................. 52-5298

[51] Int. Cl.$^2$ ................... A61K 31/19; A61K 31/215
[52] U.S. Cl. .................................... 414/317; 424/305
[58] Field of Search ................................ 424/305, 317

[56] References Cited
U.S. PATENT DOCUMENTS 4,055,589  10/1977  Inakai et al. ......................... 560/121

Primary Examiner—Sam Rosen
Attorney, Agent, or Firm—Burgess, Ryan and Wayne

[57] ABSTRACT

A pharmaceutical composition for rectal administration containing 11α,15(S)-dihydroxy-20-methoxy-16(S)-methyl-9-oxo-5(cis,13(trans)-prostadienoic acid or a water-soluble salt thereof dissolved or dispersed in a lipophilic or hydrophilic base in the presence or absence of a buffer solution or an aqueous organic amine solution.

9 Claims, No Drawings

PHARMACEUTICAL COMPOSITIONS OF A PROSTAGLANDIN COMPOUND FOR RECTAL USE IN TREATING ASTHMA

DETAILED DESCRIPTION OF THE INVENTION

The present invention relates to a pharmaceutical composition of prostaglandin derivative for rectal administration. More particularly, the invention relates to a novel pharmaceutical composition for rectal administration prepared by dissolving or dispersing 11α,15(S)-dihydroxy-20-methoxy-16(S)-methyl-9-oxo-5(cis),13(trans)-prostadienoic acid shown by formula I

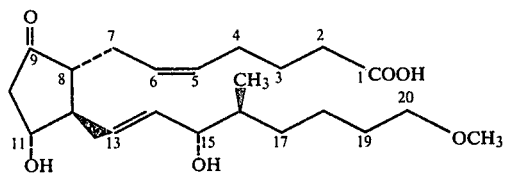

or a water-soluble salt thereof in a lipophilic or hydrophilic base in the presence or absence of a buffer solution or an aqueous organic amine solution.

The compound of formula I is a medicament useful for the treatment of bronchial asthma, which shows excellent antiasthmatic effect by an aerosol administration or oral administration and possesses unexpected advantages as compared with known 20-methoxyprostaglandin $E_2$ (11α,15(S)-dihydroxy-20-methoxy-9-oxo-5(cis),13(trans)-prostadienoic acid) which does not show antiasthmatic effect by oral administration (see, Belgian Pat. No. 836,890; German Offenlegungsschrift No. 2,555,516 and U.S. Pat. No. 4,055,589).

The pharmacological activities of the compound of this invention was tested in comparison with those of natural prostaglandin, the 16-methyl derivative thereof, and the 20-methoxy derivative thereof. The results are shown in Table I.

Experimental Procedure

I. Antiasthmatic Effect (i) Aerosol

Guinea-pigs were placed in a chamber and sprayed for 10 sec. with an aerosol of histamine solution (0.1%) and onset of sneezing was recorded. Animals that sneezed within 70–100 sec. were selected as controls. These animals were sprayed for 15 sec. with an aerosol of the test compounds. After 45 sec., the animals were sprayed with histamine and observed for 3 min. If an animal did not show sneezing within 3 min., then the tested compound was decided effective, and the percent of animals protected against sneezing was determined.

(ii) Oral

Guinea-pigs were sprayed for 10 sec with histamine 30 min after oral administration of the test compounds and observed for 3 min. The percent of amimals protected was determined.

II. Diarrhea-producing Effect

Test compounds were administered orally to guinea-pigs. The appearance of diarrhea (loose or watery feces) at every 2 hrs, 3 hrs, 4 hrs and 5 hrs period and next morning were noted. The percent of animals exhibiting diarrhea was determined.

III. Effect on Air-way Resistance

The air-way resistance of the guinea-pig lung was determined by the method of Konzett and Rössler (Arch. exp. Path. Pharmak., 195, 71–74(1940)). The bronchodilator activity of prostaglandins were expressed in terms of protective effect against bronchoconstriction induced by intravenous injection of histamine (3 μg/kg). Histamine was injected 30 min after intraduodenal administration of test compound to urethane anesthetized and artificially ventilated guinea-pigs.

TABLE 1

| Test material | Antiasthmatic effect | | | | |
|---|---|---|---|---|---|
| | Aerosol $ED_{50}$ μg/ml | Oral (a) $ED_{50}$ μg/kg | (A) (b) | b/a | (B) $ED_{50}$ μg/kg |
| Known compound Prostaglandin $E_2$ (PGE$_2$) | 0.15 | >800 | — | — | >800 |
| 11α,15(S)-dihydroxy-20-methoxy-9-oxo-5(cis)-13(trans)Prostadienoic acid (20-methoxy-PGE$_2$) | 0.15 | >800 | — | — | — |
| 11α,15(S)-dihydroxy-16(R)-methyl-9-oxo-5(cis)-13(trans)prostadienoic acid (16(R)-methyl-PGE$_2$) | 0.011 | 17.5 | 25 | 1.43 | — |
| 11α, 15(S)-dihydroxy-16(S)-methyl-9-oxo-5(cis)-13(trans)prostadienoic acid (16(S)-methyl-PGE$_2$) | 0.009 | 25 | 100 | 4.0 | — |
| Compound of this invention 11α,15(S)-dihydroxy-20-methoxy-16-methyl-9-oxo-5(cis)-13(trans)prostadienoic acid showing $[α]^{25}_D$ −65.0° (c = 0.5, chloroform) Example 6 | — | 710 | 140 | 20.0 | — |

TABLE 1-continued

| Test material | Antiasthmatic effect | | | | |
|---|---|---|---|---|---|
| | Aerosol ED$_{50}$ µg/ml | Oral (a) ED$_{50}$ µg/kg | (A) (b) | b/a | (B) ED$_{50}$ µg/kg |
| (20-methoxy-16(S)-methyl-PGE$_2$) | | | | | |

(A): Diarrhea-producing effect
(B): Effect on air-way resistance

The compound of formula I has an excellent pharmaceutical effect but the effective amount (ED$_{50}$) of the compound required for 50% inhibition of the respiratory tract contraction induced by hystamine in the case of oral administration requires about 2400 times the amount thereof as compared with the case of an intraveous injection, which is quite uneconomical. Also, in the case of using the compound as an inhalant (aerosol), it is difficult to maintain the stability of the medicament and hence the application of the compound for the purpose is practically difficult.

As the result of investigations on overcoming the aforesaid difficulties and developing a pharmaceutical composition which can be easily applied to both infants and aged, the inventors have discovered that when the compound of formula I is used as a pharmaceutical composition for rectal administration which has never been attempted in the field of pharmaceutical compositions of prostaglandin since prostaglandin and derivatives thereof are liable to adversely cause diarrhea, the compound is unexpectedly absorbed through the intestine and exhibits an antitussive effect and does not cause diarrhea. That is, a pharmaceutical composition of prostaglandin for rectal administration has first been developed by the present invention. Furthermore, according to this invention, a sufficient pharmaceutical effect is obtained with a lesser amount than that of oral administration, therefore an antiasthmatic agent is profitably provided at a low cost.

The oily bases used in this invention are such bases that are used for the preparation of ordinary ointments, suppositories, etc. with no pharmaceutical activity by themselves. Practical examples of these oily bases are, for example, fats and oils such as peanut oil, coconut oil, olive oil, soybean oil, rapeseed oil, cotton seed oil, sesame oil, corn oil, rice bran oil, tsubaki oil (from Camellia japonica L), cacao butter, lard, wool fat etc.; such fats and oils may be modified by hydrogenation, acetylation, fractional extraction, etc.; esters if fatty acids having 6–30 carbon atoms and glycerol (e.g., "Witepsol" a registered trade mark, made by Dynamit Nobel Co. and "ODO-1" a registered trade mark, made by Nisshin Seiyu K. K.); and esters of fatty acids having 6–30 carbon atoms and alcohols having 2–8 carbon atoms such as, for example, isopropyl myristate (e.g., Nikkol IPM, a registered trade mark (EX), made by Nikko Chemicals Co.).

These fats and oils may be used individually or as a mixture of two or more materials. Particularly preferred oily bases are corn oil, olive oil, and Witepsol ®.

Similarly, examples of water-soluble bases are polyethylene glycol 300, 400, 1000, 1500, 4000, and 6000 (Merck Index, 9th ed., 7349(1976)); methyl cellulose (e.g., "Metholose SM", a registered trade mark, made by Shinetsu Kagaku K. K.); carboxymethyl cellulose (Merck Index, 9th ed., 8341(1976); and glycerinated gelatin (U.S. Pharmacopoeia, 18th ed., 1970) and these water-soluble bases can be also used singly or a mixture thereof. Examples of the particularly preferred water-soluble bases are a mixture of polyethylene glycol 1000 and polyethylene glycol 4000.

Then, examples of the acids and bases for forming the buffer solution used in this invention are mixtures of acids and bases such as potassium dihydrogenphosphate, sodium dihydrogenphosphate, dipotassium hydrogenphosphate, disodium hydrogenphosphate, borax, sodium hydrogencarbonate, citric acid, disodium hydrogencitrate, potassium dihydrogencitrate, glycine, sodium chloride, potassium chloride, hydrochloric acid, sodium hydroxide, tartaric acid, sodium tartrate, lactic acid, sodium lactate, acetic acid, sodium acetate, ammonium hydroxide, ammonium chloride, dimethylglycine, etc. By properly combining these acids and bases, a buffer solution having 6–8 pH is prepared for use in this invention. The combinations of the acids and bases which are most frequently used are the combinations of sodium hydrogen-carbonate and potassium dihydrogenphosphate, citric acid and dipotassium hydrogenphosphate, disodium hydrogencitrate and sodium hydroxide, potassium dihydrogenphosphate and disodium hydrogenphosphate, borax and hydrochloric acid, and borax and potassium dihydrogenphosphate.

Examples of the organic amines used in this invention are primary amines shown by general formula $C_nH_{2n+1}NH_2$ (n=0–4) secondary amines shown by general formula $(C_nH_{2n+1})_2NH$ (n=1–4) tertiary amines shown by general formula $(C_nH_{2n+1})_3N$ (n=1–4) diamines shown by general formula $H_2N(CH_2)_mNH_2$ (m=1–4) ethanolamines shown by general formula $(HOCH_2CH_2)_pNH_{(3-p)}$ (p=1 or 2) and tris(hydroxymethylamino)methane.

At the practice of this invention, after fusing the aforesaid oily base or water-soluble base, the compound of formula I or a solution of the compound of formula I in the buffer solution or the aqueous organic amine solution is dissolved or dispersed in the fused base and then the solution or the dispersion is formed into a desired form according to a known manner of preparing ointments, suppositories, etc. In addition, a dispersing agent (e.g., a surface active agent), a stabilizer (e.g., an antioxidant, ethylenediaminetetraacetic acid, etc.,), an antiseptic, etc., may be added thereto if necessary.

The form of the pharmaceutical compositions for rectal administration of this invention may be a conventional suppository which is in a solid state at normal temperature but is fused at body temperature, an ointment prepared by dispersing the pharmaceutical composition in a liquid fat or oil, a liquid enema such as soft capsules for rectal administration, or a liquid composition which is administrated using a clyster-pipe for rectal use.

The amount of the acid and the base for forming the buffer solution is 0.1–100,000 mole times, more preferably 1–1,000 mole times the amount of the compound of formula I. Also, the amount of the organic amine used in this invention is 0.1–100,000 mole times, more preferably 1–1,000 mole times the amount of the compound of formula I. Furthermore, the amount of the oily base or the water-soluble base is 1,000–10,000,000 times, more preferably 10,000–1,000,000 times the weight of the compound of formula I.

Then, the following experiments and examples illustrate, respectively, the excellent effectiveness of the pharmaceutical compositions for rectal administration of this invention and the production processes of the pharmaceutical compositions for rectal administration of this invention.

Experiment 1

A suppository prepared using the compound of formula I and the oily base or water-soluble base was applied by rectal administration (this invention) to male guinea pigs fasted for 24 hours, each weighing about 550 g. On the other hand, a solution of the compound of formula I in physiological saline solution was applied by oral administration to guinea pigs under the same condition as above for control. After 30 minutes from the administration, the bronchodilator activity of the medicament was determined by a histamine spray method. The results are shown in Table II.

Table II
Bronchodilator activity of the rectal pharmaceutical composition of the compound of formula I.

| Dose ($\mu$g/kg) | Oral administration (control) | Witepsol suppository Example No. | Polyethylene glycol suppository Example No. |
|---|---|---|---|
| 0.25 |  | 1/6   1 |  |
| 0.5 |  | 1/6   2 | 1/6   7 |
| 1 |  | 3/6   3 |  |
| 2 |  | 4/6   4 |  |
| 3.1 | 1/6 |  |  |
| 4 |  | 4/6   5 |  |
| 6.3 | 3/6 |  |  |
| 8 |  | 5/6   6 |  |
| 12.5 | 4/6 |  |  |
| 25 | 4/6 |  |  |
| 50 | 5/6 |  |  |
| ED$_{50}$($\mu$g/kg) | 7.0 | 1.5 |  |

The numerator number shows the effective examples and the denominator number shows the animal numbers tested in one group.

As is clear from the results shown in Table II, the effect was increased by the use of the Witepsol suppositories (Examples 1–6 of this invention) to about 4.6 times than that of by the oral administration (control). The use of the polyethylene glycol suppository (Example 7 of this invention) showed the almost similar effect to in the case of using the Witepsol suppositories.

Experiment 2

Suppositories prepared by dispersing the compound of formula I in oily bases together with the buffer solution (Examples 8–12 of this invention) or the aqueous organic amine solution thereof (Examples 13–16 of this invention) were applied by rectal administration and then the bronchodilating actions were determined by the same manner as in Experiment 1. The results are shown in Table III.

Table III
Bronchodilator activity in the case of the rectal compositions prepared from the buffer solution or organic amine solution of the compound of formula I.

| Dose ($\mu$g/kg) | Buffer solution Example No. | Organic amine solution Example No. |
|---|---|---|
| 0.125 | 0/6   8 | 1/6   13 |
| 0.25 | 2/6   9 | 1/6   14 |
| 0.5 | 3/6   10 | 2/6   15 |
| 1 | 4/6   11 | 4/6   16 |
| 2 | 4/6   12 |  |
| ED$_{50}$ ($\mu$g/kg) | 0.65 | 0.68 |

The numerator number shows the effective examples and the denominator number shows the animal numbers tested in one group.

As is clear from the results shown in Table III, when the suppositories prepared using the buffer solution or aqueous organic amine solution of the compound of formula I were used, the effect was increased to about 10 times than that of by oral administration.

EXAMPLE 1

After fusing 4.92 g. of Witepsol W-35 ® at 50° C., 0.1 ml. of an ethanol solution containing 20 $\mu$g. of the compound of formula I was added to it, followed by stirring sufficiently and 500 mg of aliquots of the mixture were poured into a mold for suppositories. After solidified, the suppositories formed were released from the mold.

EXAMPLE 2

After fusing 4.92 g. of Witepsol W-35 ® at about 50° C., 0.1 ml. of an ethanol solution containing 5 $\mu$g. of the compound of formula I was added to it, followed by stirring sufficiently and 500 mg. of aliquots of the mixture were poured into a mold for suppositories. After solidified, the suppositories formed were released from the mold.

EXAMPLE 3

After fusing 4.92 g. of Witepsol W-35 ® at about 50° C., 0.1 ml of an ethanol solution containing 10 $\mu$g. of the compound of formula I was added to it, followed by stirring sufficiently and 500 mg. of aliquots of the mixture were poured into a mold for suppositories. After solidified, the suppositories formed were released from the mold.

EXAMPLE 4

After fusing 4.92 g. of Witepsol W-35 ® at about 50° C., 0.1 ml. of an ethanol solution containing 20 $\mu$g. of the compound of formula I was added to it, followed by stirring sufficiently and 500 mg. of aliquots of the mixture were poured into a mold for suppositories. After solidified, the suppositories formed were released from the mold.

EXAMPLE 5

After fusing 4.92 g. of Witepsol W-35 ® at about 50° C., 0.1 ml. of an ethanol solution containing 40 $\mu$g. of the compound of formula I was added to it, followed by stirring sufficiently and 500 mg. of aliquots of the mixture were poured into a mold for suppositories. After solidified, the suppositories formed were released from the mold.

EXAMPLE 6

After fusing 4.92 g. of Witepsol W-35 ® at about 50° C., 0.1 ml. of an ethanol solution containing 80 μg. of the compound of formula I was added to it, followed by stirring sufficiently and 500 mg. of aliquots of the mixture were poured into a mold for suppositories. After solidified, the suppositories formed were released from the mold.

EXAMPLE 7

After fusing 4.37 g. of polyethylene glycol 1000 and 0.55 g. of polyethylene glycol 4000, 0.1 ml. of an ethanol solution containing 5 μg. of the compound of formula I was added thereto, followed by stirring sufficiently and 500 mg. of aliquots of the mixture were poured into a mold for suppositories. After solidified, the suppositories formed were released from the mold.

EXAMPLE 8

After fusing 4.90 g. of Witepsol W-35 ® at about 50° C., 0.1 ml. of a buffer solution ($8.5 \times 10^{-2}$ mole/liter of each of sodium hydrogencarbonate and potassium dihydrogenphosphate) containing 1.25 μg. of the compound of formula I was dispersed therein with stirring well and 500 mg. of aliquots of the dispersion were poured into a mold for suppositories. After solidified, the suppositories formed were released from the mold.

EXAMPLE 9

After fusing 4.90 g. of Witepsol W-35 ® at about 50° C., 0.1 ml. of a buffer solution ($8.5 \times 10^{-2}$ mole/liter of each of sodium hydrogencarbonate and potassium dihydrogenphosphate) containing 2.5 μg. of the compound of formula I was dispersed therein with stirring well and 500 mg. of aliquots of the dispersion were poured into a mold for suppositories. After solidified, the suppositories formed were released from the mold.

EXAMPLE 10

After fusing 4.90 g. of Witepsol W-35 ® at about 50° C., 0.1 ml. of a buffer solution ($8.5 \times 10^{-2}$ mole/liter of each of sodium hydrogencarbonate and potassium dihydrogenphosphate) containing 5 μg. of the compound of formula I was dispersed therein with stirring well and 500 mg. of aliquots of the dispersion were poured into a mold for suppositories. After solidified, the suppositories formed were released from the mold.

EXAMPLE 11

After fusing 4.90 g. of Witepsol W-35 ® at about 50° C., 0.1 ml. of a buffer solution ($8.5 \times 10^{-2}$ mole/liter of each of sodium hydrogencarbonate and potassium dihydrogenphosphate) containing b 1 μg. of the compound of formula I was dispersed therein with stirring well and 500 mg. of aliquots of the dispersion were poured into a mold for suppositories. After solidified, the suppositories formed were released from the mold.

EXAMPLE 12

After fusing 4.90 g. of Witepsol W-35 ® at about 50° C., 0.1 ml. of a buffer solution ($8.5 \times 10^{-2}$ mole/liter of each of sodium hydrogencarbonate and potassium dihydrogenphosphate) containing 2 μg. of the compound of formula I was dispersed therein with stirring well and 500 mg. of aliquots of the dispersion were poured into a mold for suppositories. After solidified, the suppositories formed were released from the mold.

EXAMPLE 13

After fusing 4.90 g. of Witepsol W-35 ® at about 50° C., 0.1 ml. of an aqueous tris(hydroxymethylamino)methane solution ($5.3 \times 10^{-4}$ mole/liter) containing 1.25 μg. of the compound of formula I was dispersed therein with stirring well and 500 mg. of aliquots of the dispersion were poured into a mold for suppositories. After solidified, the suppositories formed were released from the mold.

EXAMPLE 14

After fusing 4.90 g. of Witepsol W-35 ® at about 50° C., 0.1 ml. of an aqueous tris(hydroxymethylamino)methane solution ($1.1 \times 10^{-3}$ mole/liter) containing 2.5 μg. of the compound of formula I was dispersed therein with stirring well and 500 mg. of aliquots of the dispersion were poured into a mold for suppositories. After solidified, the suppositories formed were released from the mold.

EXAMPLE 15

After fusing 4.90 g. of Witepsol W-35 ® at about 50° C., 0.1 ml. of an aqueous tris(hydroxymethylamino)methane solution ($2.1 \times 10^{-3}$ mole/liter) containing 5 μg. of the compound of formula I was dispersed therein with stirring well and 500 mg. of aliquots of the dispersion were poured into a mold for suppositories. After solidified, the suppositories formed were released from the mold.

EXAMPLE 16

After fusing 4.90 g. of Witepsol W-35 ® at about 50° C., 0.1 ml. of an aqueous tris(hydroxymethylamino)methane ($4.2 \times 10^{-3}$ mole/liter) containing 10 μg. of the compound of formula I was dispersed therein with stirring well and 500 mg. of aliquots of the dispersion formed were poured into a mold for suppositories. After solidified, the suppositories formed were released from the mold.

EXAMPLE 17

After adding 0.1 ml. of an ethanol solution containing 20 μg. of the compound of formula I to 4.90 g. of corn oil followed by stirring sufficiently, 300 mg. of aliquots of the mixture were poured into clyster-pipe for rectal administration.

EXAMPLE 18

After fusing 4.90 g. of Witepsol W-35 ® at about 50° C., 0.1 ml. of a buffer solution ($2.6 \times 10^{-2}$ mole/liter of citric acid and $1.11 \times 10^{-1}$ mole/liter of dipotassium hydrogenphosphate) containing 10 μg. of the compound of formula I was dispersed therein with stirring well and 500 mg. of aliquots of the dispersion were poured into a mold for suppositories. After solidified, the suppositories formed were released from the mold.

EXAMPLE 19

After fusing 4.90 g. of Witepsol W-35 ® at about 50° C., 0.1 ml. of an aqueous ethanolamine solution ($4.2 \times 10^{-3}$ mole/liter) containing 10 μg. of the compound of formula I was dispersed therein with stirring well and 500 mg. of aliquots of the dispersion were poured into a mold for suppositories. After solidified, the suppositories formed were released from the mold.

What is claimed is:

1. A method of treating bronchial asthma comprising rectally administering an effective amount of a composition which comprises 11α,15(S)-Dihydroxy-20-methoxy-16(S)-methyl-9-oxo-5(cis),13(trans)-prostadienoic acid represented by the formula

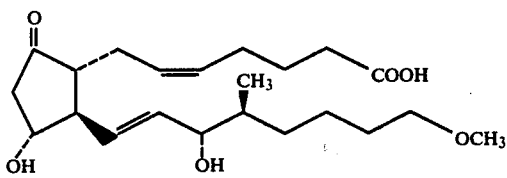

dissolved or dispersed in a lipophilic or hydrophilic base.

2. A method as claimed in claim 1 wherein the hydrophilic base is a member selected from the group consisting of polyethylene glycol, methylcellulose, sodium carboxymethylcellulose and glycerinated gelatin.

3. A method as claimed in claim 1, wherein said composition further comprises a buffer solution or an aqueous organic amine solution.

4. A method as claimed in claim 1, wherein said composition further comprises at least one additive selected from the group consisting of dispersing agents, stabilizers, and antiseptics.

5. A method as claimed in claim 1, wherein said composition is in the form of a suppository.

6. A method as claimed in claim 1, wherein said effective amount is from 0.25 to 8 μg/kg.

7. A method as claimed in claim 3, wherein said effective amount is from 0.125 to 2 μg/kg.

8. A method as claimed in claim 3 wherein the buffer solution is a member selected from the group consisting of sodium hydrogen carbonate and potassium dihydrogenphosphate, citric acid and dipotassium hydrogenphosphate, disodium hydrogencitrate and sodium hydroxide, potassium dihydrogenphosphate and dipotassium hydrogenphosphate, borax and hydrochloric acid, and borax and potassium dihydrogenphosphate.

9. A method as claimed in claim 3 wherein the organic amine is a member selected from the group consisting of primary amine shown by the general formula $C_nH_{2n+1}NH_2$ (n=0–4), secondary amine shown by the general formula $(C_nH_{2n+1})_2NH$ (n=1–4), tertiary amine shown by the general formula $(C_nH_{2n+1})_3N$ (n=1–4), diamine shown by the general formula $H_2N(CH_2)_mNH_2$ (m=1–4), ethanolamine shown by the general formula $(HOCH_2CH_2)_pNH_{(3-p)}$ (p=1 or 2) and tris(hydroxymethylamino)methane.

* * * * *